US007998056B2

(12) United States Patent
Stifter et al.

(10) Patent No.: US 7,998,056 B2
(45) Date of Patent: Aug. 16, 2011

(54) TRAINING DEVICE FOR THE MUSCLES OF THE PELVIC FLOOR

(76) Inventors: Karl Stifter, Vienna (AT); Gerhard Bruckberger, Vienna (AT)

( * ) Notice: Subject to any disclaimer, the term of this patent is extended or adjusted under 35 U.S.C. 154(b) by 1096 days.

(21) Appl. No.: 10/587,176

(22) PCT Filed: Jan. 20, 2005
(Under 37 CFR 1.47)

(86) PCT No.: PCT/AT2005/000009

§ 371 (c)(1),
(2), (4) Date: Jun. 15, 2007

(87) PCT Pub. No.: WO2005/070504

PCT Pub. Date: Aug. 4, 2005

(65) Prior Publication Data

US 2008/0249353 A1 Oct. 9, 2008

(30) Foreign Application Priority Data

Jan. 27, 2004 (AT) .................................. A 107/2004
Jan. 27, 2004 (AT) .................................. GM50/2004

(51) Int. Cl.
*A61F 5/00* (2006.01)

(52) U.S. Cl. ......................................................... 600/38

(58) Field of Classification Search .............. 600/38-41, 600/500, 29-32; D24/133, 135, 214
See application file for complete search history.

(56) References Cited

U.S. PATENT DOCUMENTS

| | | | | |
|---|---|---|---|---|
| 1,628,272 A | | 5/1927 | Reitz | |
| 2,763,265 A | | 9/1956 | Waters | |
| 4,881,526 A | | 11/1989 | Johnson et al. | |
| 5,931,775 A | * | 8/1999 | Smith | 600/29 |
| D458,681 S | * | 6/2002 | Sherlock et al. | D24/141 |
| 6,562,018 B1 | * | 5/2003 | Russell | 604/500 |
| D590,066 S | * | 4/2009 | Stewart | D24/214 |

FOREIGN PATENT DOCUMENTS

| | | |
|---|---|---|
| DE | 299 10 732 | 2/2000 |
| WO | 03/089071 | 10/2003 |

* cited by examiner

*Primary Examiner* — Samuel Gilbert
(74) *Attorney, Agent, or Firm* — Dykema Gossett PLLC

(57) ABSTRACT

The invention relates to a training device, for the muscles of the pelvic floor in women, comprising a flexible main body (1), for introduction into the vagina and which has a compression piece (1) with a spherical working surface (2). According to the invention, an substantial improvement in the training effect can be achieved, whereby the compression piece (1) is defined by two annular constrictions (3, 5), connected axially on one side to a stop section (4) with a stop surface and connected axially on the other side to a retainer section (6) to which a display is fixed.

9 Claims, 1 Drawing Sheet

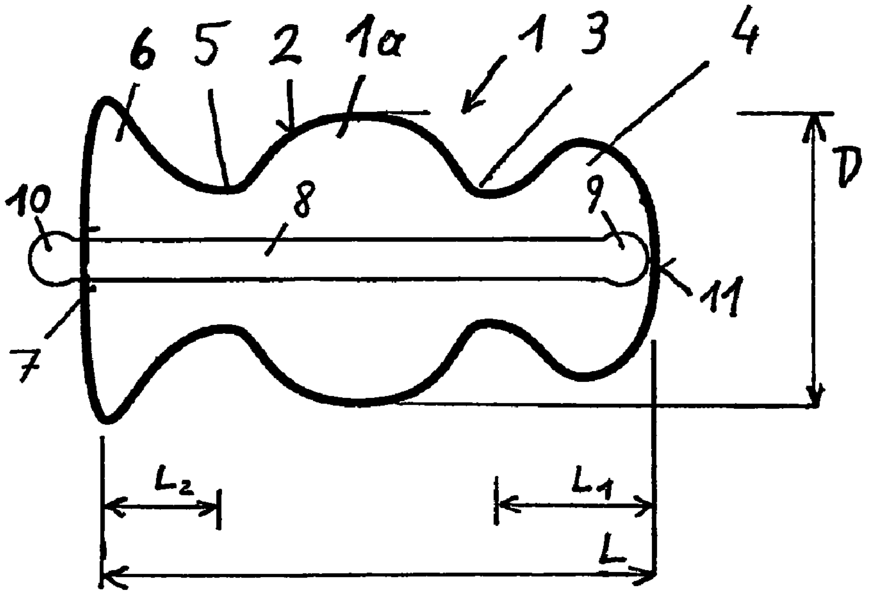
FIG..1
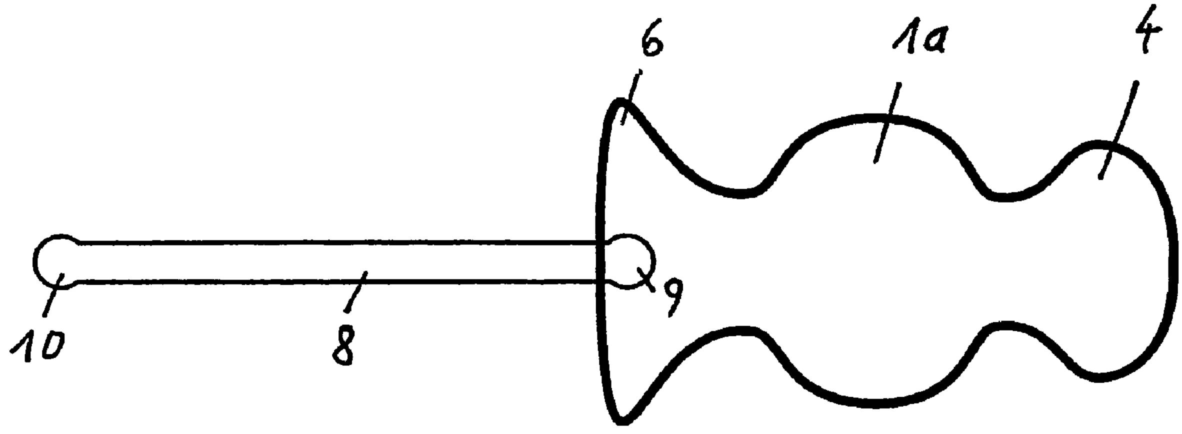
FIG..2

TRAINING DEVICE FOR THE MUSCLES OF THE PELVIC FLOOR

BACKGROUND OF THE INVENTION

1. Field of the Invention

The invention relates to a training device for the muscles of the pelvic floor of women.

2. The Prior Art

It is well known that for women sexual fulfillment in coitus is largely dependent on the state and control of the muscles of the pelvic floor. Various attempts have been made to train these muscles by means of devices which are introduced into the vagina. In this context diverse problems have arisen which have not be solved satisfactorily with the known devices and apparatus. On the one hand such devices should permit and encourage the active and conscious moving of the muscles, while simultaneously providing the possibility for the woman to control or monitor the training situation. The particular aim of the training is to enable the woman to consciously and selectively tense and relax muscles, since studies have shown that without relevant training, about 50% of all women are not able to identify the muscles of this region from verbal instruction alone. On the other hand, such devices should meet strict hygienic requirements even when used in the home, and still be affordable.

From WO 03/089071 A a training device is known which has a pear-shaped main body. It has been found that this device cannot guarantee an optimum training effect for the local muscles.

It is the object of the present invention to further develop such a device in order to attain an improved effect while avoiding the disadvantages mentioned above.

SUMMARY OF THE INVENTION

The invention proposes that the compression part be defined by two annular constrictions which connect axially on one side to a stop section with a stop surface and on the other side to a holding section, to which an indicator device is attached in turn. In this way the region of the compression part having the largest diameter, i.e., the equatorial line, is farther distant from the stop surface, and the muscles can obtain a firm grip in the first constriction. Furthermore, it is thus possible to configure the stop surface with a large flat area.

The device according to the invention permits training of the muscles of the pelvic floor in a simple and controllable manner. It is essential that insertion of the device is limited by the stop surface, whose distance from the compression part is chosen such that the ball-shaped working surface of the compression part is positioned exactly in the area of the muscle groups to be trained. Since the vaginal wall will envelop the working surface of the compression part on both sides of the equatorial line essentially symmetrically, a contraction of the muscles will result in an inwardly directed deformation of the compression part, while no significant axial force will be exerted on the training device. The training device is gripped and meets the force exerted from outside with a corresponding resisting force whose strength depends on the pressure applied to the compression part. Working against this resisting force produces the desired training effect, which strengthens the relevant group of muscles. When the muscles are relaxed, e.g. when the training session is finished, the device may easily be withdrawn and removed.

It is an essential feature of the device that the indicator device permits monitoring of the exercises and progress in the training activity in a simple way. If the muscles are correctly tensed, the main body undergoes a deformation causing a tilting movement of the indicator device, with an axial movement added in certain cases. By these movements the deformation of the main body can be registered in an optical and tactile way, and the actual muscle contraction may be inferred.

It has been found to be of particular advantage if the working surface is essentially spherical. This will provide optimum geometrical conditions.

The training effect will be especially efficient if the axial length of the stop section is between 40% and 65% of the maximum diameter of the compression part. In this context it will be particularly advantageous if the axial length of the holding section is between 30% and 60% of the maximum diameter of the compression part.

A particularly advantageous variant of the invention will result if the indicator device is configured as a withdrawable rod. It is especially advantageous if the rod is held in an opening of the holding section in such a manner that it may be shifted within certain limits. While efficiently serving to indicate muscular tension this will permit a simple design with low manufacturing costs.

As regards design simplicity and low manufacturing costs it is furthermore of advantage if the main body is configured as a rubber bubble which is covered with a gliding layer, the gliding layer consisting of loose fibres which are steeped in a gliding agent.

From the hygienic point of view it is of particular advantage if the training device is designed as a throw-away product.

The invention will now be described in more detail with reference to the embodiment shown in the enclosed drawings.

FIG. 1 shows a training device according to the invention, with the rod inserted in the device; and FIG. 2 shows the training device of FIG. 1 with the rod withdrawn.

DETAILED DESCRIPTION OF THE PREFERRED EMBODIMENT

The training device shown in the drawings consists of a main body 1 with a compression part 1*a* having a working surface 2 on its outside. In axial direction the compression part 1*a* on one side is followed by a first constriction 3, which in turn continues to a stop section 4. On the opposite side of the stop section 4 the compression part 1*a* is followed by a second constriction 5 adjacent to a holding section 6.

The compression part 1*a* is essentially spherical and has a diameter D, which is adapted to the anatomy of the woman; the training device may thus be marketed in two or more sizes, e.g., one size for women who have already given birth and another size for women who have not done so. The total length L of the device is about 1.8 D, with the length $L_1$ of the stop section being 0.5 D and the length $L_2$ of the holding section being 0.4 D. In an opening 7 of the holding section 6 a withdrawable rod 8 (indicator device) is held in such a way that it can be axially shifted. The rod 8 has a first thickening 9 at one end, which is placed inside the training device and prevents the complete withdrawal of the rod. At the other end of the rod a second thickening 10 is provided, which will permit better gripping and holding of the rod 8 in a simple manner.

The use of the training device according to the invention will now be explained. The training device is inserted into the vagina with the stop section 4 foremost, until the stop surface 11 of the stop section 4 touches in the region of the portio vaginalis cervicis. In this position the tunica muscularis of the vagina envelops the working surface 2 of the main body 1 and is distended radially outwards by the compression part 1*a*. By tensing these muscles the compression part 1*a* may be contracted against its deformation resistance, thus producing the desired training effect. The tension of the muscles can be monitored via the movement of the rod 8 caused by the deformation of the main body 1, the rod 8 thus acting as an indicator.

In the inserted state the second constriction 5 is situated in the region of the vaginal entrance and the holding section 6 is completely outside the female body. This will substantially facilitate withdrawal of the training device.

The training device is made from a rubber bubble in order to enable a suitable deformation. Insertion into the vaginal region is eased by a gliding layer, which is applied to the rubber bubble and consists of a loose layer of fibres steeped in a gliding agent. Preferably, the training device is a throw-away product in order to conform to strict requirements of hygiene. Multiple use of the device in contravention of hygienic rules is prevented or at least significantly impeded by the fact that the gliding layer is largely destroyed after first use, thus prohibiting further use.

The training device according to the invention permits specific training of the muscles of the pelvic floor and will thus lead to a significant enhancement of sensation during coitus. In addition, advantageous effects are observed with regard to the avoidance of incontinence problems.

The invention claimed is:

1. A training device for the muscles of the pelvic floor of women, comprising a flexible main body which is to be at least partially inserted into the vagina and which has a compression part with a ball-shaped working surface, the compression part being defined by two annular constrictions, the main body extending axially to a stop section with a stop surface on one side of the compression part and to a holding section on an opposite side of the compression part, the holding section defining an opening, and an indicator rod which extends through said opening so as to be connected to said main body, said indicator rod being movable toward and away from said stop surface.

2. The training device according to claim 1, wherein the working surface is essentially spherical.

3. The training device according to claim 1, wherein an axial length of the stop section is between 40% and 65% of a maximum diameter of the compression part.

4. The training device according to claim 1, wherein an axial length of the holding section is between 30% and 60% of a maximum diameter of the compression part.

5. The training device according to claim 1, wherein the main body is configured as a rubber bubble, which is covered by a gliding layer.

6. The training device according to claim 5, wherein the gliding layer consists of a layer of loose fibers steeped in a gliding agent.

7. The training device according to claim 1, wherein the training device is designed as a throw-away product.

8. The training device according to claim 1, wherein the indicator rod includes enlarged ends.

9. A training device for the muscles of the pelvic floor of women, comprising a flexible main body which is to be at least partially inserted into the vagina and which has a compression part with a ball-shaped working surface, the compression part being defined by two annular constrictions, the main body extending axially to a stop section with a stop surface on one side of the compression part and to a holding section on an opposite side of the compression part, the main body comprising a rubber bubble covered by a gliding layer consisting of loose fibers steeped in a gliding agent, and an indicator device attached to the main body.

* * * * *